(12) United States Patent
Satou et al.

(10) Patent No.: US 7,125,692 B2
(45) Date of Patent: Oct. 24, 2006

(54) PROCESS FOR PRODUCING MONOMER

(75) Inventors: Eiji Satou, Kanagawa (JP); Makoto Kaneko, Kanagawa (JP); Naoshi Murata, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/488,253

(22) PCT Filed: Sep. 11, 2002

(86) PCT No.: PCT/JP02/09271

§ 371 (c)(1),
(2), (4) Date: Mar. 11, 2004

(87) PCT Pub. No.: WO03/025194

PCT Pub. Date: Mar. 27, 2003

(65) Prior Publication Data
US 2004/0236051 A1 Nov. 25, 2004

(30) Foreign Application Priority Data
Sep. 12, 2001 (JP) ............... 2001-277210

(51) Int. Cl.
C07P 17/04 (2006.01)
C07P 17/06 (2006.01)
(52) U.S. Cl. .............. 435/126; 435/124; 435/125; 435/127
(58) Field of Classification Search .......... 549/313; 435/123, 124, 125, 126, 127
See application file for complete search history.

(56) References Cited

FOREIGN PATENT DOCUMENTS

| EP | 0 439 779 | 8/1991 |
|----|-----------|--------|
| EP | 514694 | 11/1992 |
| JP | 4-279576 | 10/1992 |
| JP | 5-219970 | 8/1993 |
| JP | 10-212283 | 8/1998 |
| JP | 2001-235867 | 8/2001 |
| JP | 2001-247513 | 9/2001 |

OTHER PUBLICATIONS

Koji Nozaki, et al., "A new single-layer resist for 193-nm lithography", Jpn, J. Appl. Phys., vol. 35, No. 4B, pp.: L528-530 Apr. 15, 1996.

*Primary Examiner*—Bernard Dentz
(74) *Attorney, Agent, or Firm*—Oblon, Spivak, McClelland, Maier & Neustadt, P.C.

(57) ABSTRACT

A process for producing a monomer for resists represented by the following general formula 1:

$$\text{(1)}$$

wherein $R^1$ represents hydrogen or an optionally substituted alkyl group; $R^2$, $R^3$ and $R^4$ each independently represent hydrogen or a substituent; and X, Y and Z each independently represent a direct bond or an optionally substituted alkylene group with 1 to 3 chain members, the process comprising carrying out esterification or transesterification in the presence of a biocatalyst.

21 Claims, No Drawings

PROCESS FOR PRODUCING MONOMER

This application is a 371 of PCT/JP02/09271 filed Sep. 11, 2002.

TECHNICAL FIELD

The present invention relates to a process for producing a monomer for resists.

BACKGROUND ART

Resists for use in microfabrication by lithography are prepared from various materials. For example, a resist for use in production of semiconductors is prepared by polymerizing one or more kinds of monomers and adding an additive, acid generating agent, solvent or the like to the polymerized product. In these resists, their contamination by impurities need to be reduced as much as possible depending on the purpose. Therefore, in the production of a monomer for resists, too, it is preferable to reduce the formation of by-product.

Commonly employed processes for synthesizing esters include, for example, addition reaction of alkene and (meth)acrylic acid performed in the presence of acid catalyst; dehydration (in the presence of condensation agent or acid catalyst) of alcohol and (meth)acrylic acid; transesterification between alcohol and ester; and esterification by acid chloride.

Monomers for resists each having an alicyclic structure are three-dimensionally bulky and subject to decomposition by acid. Therefore, generally it is difficult to synthesize such monomers by addition reaction, dehydration or transesterification in the presence of acid catalyst. As a result, usually such monomers are frequently synthesized by esterification by acid chloride, as described in JPN. J. Appl. Phys. 1996, 35(4B) L 528–530. Ester synthesis by transesterification using a titanium- or tin-containing compound is also well known.

In the synthesis of monomers for resists, however, since alcohol itself used as a starting material is bulky, when conducting transesterification by the well known processes as above, the reaction is often retarded significantly or often does not progress at all due to the inactivation of catalyst and the like.

In addition, since resists prepared by chemical syntheses as described above are contaminated much by by-products or catalyst added, their purification requires great labor. In such context, an ester synthesizing process for producing monomers for resists has been desired which uses no acid catalysts, is carried out under mild conditions and makes product purification easier.

On the other hand, esterification or transesterification by enzymes is widely known. However, since enzymatic reactions are highly substrate-selective and site-selective, generally it is difficult to use enzymes in transesterification for producing bulky monomers, and there have been no examples in which enzymes are applied to special monomers of high bulk, such as monomers for resists.

DISCLOSURE OF THE INVENTION

Accordingly, the object of the present invention is to provide a process for producing a monomer for resists which uses no acid catalysts, is carried out under mild conditions, and makes product purification easier.

After directing tremendous research effort toward solving the above problem, the inventors of the present invention has found that the above problem can be solved by carrying out esterification or transesterification in the presence of a biocatalyst, and they have finally accomplished the present invention.

Specifically, the present invention encompasses the following.

(1) A process for producing a monomer for resists represented by the following general formula 1:

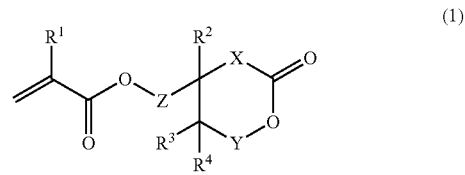

wherein $R^1$ represents hydrogen or optionally substituted alkyl group; $R^2$, $R^3$ and $R^4$ each independently represent hydrogen or a substituent; and X, Y and Z each independently represent a direct bond or optionally substituted alkylene with 1 to 3 chain members, comprising carrying out esterification or transesterification in the presence of a biocatalyst.

(2) A process for producing a monomer for resists represented by the following general formula 1,

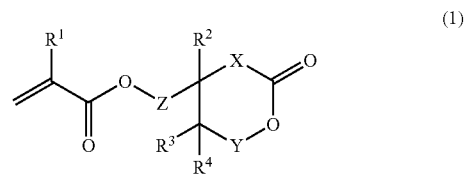

wherein $R^1$, $R^2$, $R^3$, $R^4$, X, Y and Z are defined as described above, comprising carrying out esterification or transesterification between a compound represented by the following general formula 2:

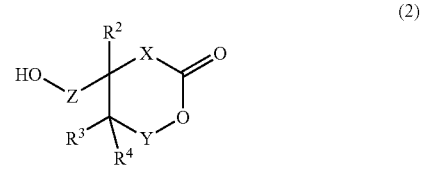

wherein $R^2$, $R^3$, $R^4$, X, Y and Z are defined as described above, and a compound represented by the following general formula 3:

wherein $R^1$ is defined as described above and $R^5$ represents hydrogen or a substituent, in the presence of a biocatalyst.

The term "transesterification" herein used means a reaction whereby an alkoxy group or acyl group of ester is replaced with another alkoxy group or acyl group.

The term "esterification" herein used means a reaction whereby acids are converted into esters.

In the following the present invention will be described in detail.

In the present invention, compounds represented by the general formula 1 are not particularly limited, as long as they function as a monomer, in other words, they are polymerizable.

In the general formulae 1 and 3, $R^1$ represents a hydrogen atom or an $C_{1-4}$ alkyl group, such as methyl group, ethyl group, propyl group, isopropyl group, butyl group and isobutyl group. The alkyl group may be substituted with substituents such as halogen atoms. Preferably, $R^1$ is a hydrogen atom or a methyl group.

In the general formulae 1 and 2, $R^2$, $R^3$ and $R^4$ each independently represent a hydrogen atom or a substituent. Specific examples of the substituents include a hydroxyl group; $C_{1-4}$ alkyl groups, such as methyl group, ethyl group, propyl group, isopropyl group, butyl group and isobutyl group; $C_{2-4}$ alkenyl groups, such as vinyl group, propenyl group and butenyl group; $C_{2-6}$ alkynyl groups, such as ethynyl group, propynyl group, butynyl group, pentynyl group and hexynyl group; $C_{1-4}$ alkoxy groups, such as methoxy group, ethoxy group, propoxy group and butoxy group; $C_{1-4}$ alkylthio groups, such as methylthio group, ethylthio group, propylthio group and butylthio group; $C_{1-7}$ amide groups, such as formamide group, acetamide group, propionamide group and hexanamide group; a cyano group; $C_{1-4}$ acyl groups, such as formyl group, acetyl group, propionyl group and butyryl group; $C_{2-4}$ alkoxycarbonyl groups, such as methoxycarbonyl group, ethoxycarbonyl group and propoxycarbonyl group; aralkyl groups such as benzyl group, phenethyl group and naphthylmethyl group; amino groups having one or more $C_{1-4}$ alkyl groups, such as methylamino group, dimethylamino group, ethylamino group, propylamino group and butylamino group; a nitro group; a thiol group; and those derived from the above substiuents. The above-described substituents, such as alkyl groups, alkenyl groups, alkynyl groups, alkoxy groups, alkylthio groups, amide groups, acyl groups, alkoxycarbonyl groups, aralkyl groups and amino groups having one or more alkyl groups, may be substituted with substituents such as halogen atoms. Preferably, $R^2$, $R^3$ and $R^4$ each are a hydrogen atom, a methyl group or an ethyl group.

X, Y and Z each independently represent a direct bond or an optionally substituted alkylene group with 1 to 3 chain members, for example, methylene, ethylene and trimethylene.

Lactone rings which include X and Y may have any one of the ring structures selected from 4 to 10 membered rings, preferably they are 5 to 6 membered rings. X and Y may also have 1 to 3 substituents of the same or different types. Specific examples of such substituents include a hydroxyl group; $C_{1-4}$ alkyl groups, such as methyl group, ethyl group, propyl group, isopropyl group, butyl group and isobutyl group; $C_{2-4}$ alkenyl groups, such as vinyl group, propenyl group and butenyl group; $C_{2-6}$ alkynyl groups, such as ethynyl group, propynyl group, butynyl group, pentynyl group and hexynyl group; $C_{1-4}$ alkoxy groups, such as methoxy group, ethoxy group, propoxy group and butoxy group; $C_{1-4}$ alkylthio groups, such as methylthio group, ethylthio group, propylthio group and butylthio group; $C_{1-7}$ amide groups, such as formamide group, acetamide group, propionamide group and hexanamide group; a cyano group; $C_{1-4}$ acyl groups, such as formyl group, acetyl group, propionyl group and butyryl group; $C_{2-4}$ alkoxycarbonyl groups, such as methoxycarbonyl group, ethoxycarbonyl group and propoxycarbonyl group; aralkyl groups such as benzyl group, phenethyl group and naphthylmethyl group; amino groups having one or more $C_{1-4}$ alkyl groups, such as methylamino group, dimethylamino group, ethylamino group, propylamino group and butylamino group; a nitro group; a thiol group; and those derived from the above substiuents. The above-described substituents, such as alkyl groups, alkenyl groups, alkynyl groups, alkoxy groups, alkylthio groups, amide groups, acyl groups, alkoxycarbonyl groups, aralkyl groups and amino groups having one or more alkyl groups, may be substituted with substituents such as halogen atoms. Preferred substituents in X and Y are a methyl group and an ethyl group.

An alkylene group with 1 to 3 chain members which is represented by Z may have 1 to 3 substituents of the same or different types. Specific examples of such substituents include a hydroxyl group; $C_{1-4}$ alkyl groups, such as methyl group, ethyl group, propyl group, isopropyl group, butyl group and isobutyl group; $C_{2-4}$ alkenyl groups, such as vinyl group, propenyl group and butenyl group; $C_{2-6}$ alkynyl groups, such as ethynyl group, propynyl group, butynyl group, pentynyl group and hexynyl group; $C_{1-4}$ alkoxy groups, such as methoxy group, ethoxy group, propoxy group and butoxy group; $C_{1-4}$ alkylthio groups, such as methylthio group, ethylthio group, propylthio group and butylthio group; $C_{1-7}$ amide groups, such as formamide group, acetamide group, propionamide group and hexanamide group; a cyano group; $C_{1-4}$ acyl groups, such as formyl group, acetyl group, propionyl group and butyryl group; $C_{2-4}$ alkoxycarbonyl groups, such as methoxycarbonyl group, ethoxycarbonyl group and propoxycarbonyl group; aralkyl groups such as benzyl group, phenethyl group and naphthylmethyl group; amino groups having one or more $C_{1-4}$ alkyl groups, such as methylamino group, dimethylamino group, ethylamino group, propylamino group and butylamino group; a nitro group; a thiol group; and those derived from the above substiuents. The above-described substituents, such as alkyl groups, alkenyl groups, alkynyl groups, alkoxy groups, alkylthio groups, amide groups, acyl groups, alkoxycarbonyl groups, aralkyl groups and amino groups having one or more alkyl groups, may be substituted with substituents such as halogen atoms. Preferred substituents in Z are a methyl group and an ethyl group.

In the general formula 3, $R^5$ represents a hydrogen atom or a substituent. Specific examples of such substituents include $C_{1-6}$ alkyl groups, such as methyl group, ethyl group, propyl group, isopropyl group, butyl group, isobutyl group, pentyl group and hexyl group; $C_{2-6}$ alkenyl groups, such as vinyl group, propenyl group, butenyl group, pentenyl group and hexenyl group; $C_{2-6}$ alkynyl groups, such as ethynyl group, propynyl group, butynyl group, pentynyl group and hexynyl group; and aralkyl groups such as benzyl group, phenethyl group and naphthylmethyl group. The above-described substituents, such as alkyl groups, alkenyl groups, alkynyl groups and aralkyl groups may be substituted with substituents such as $C_{1-4}$ alkoxy groups, $C_{1-4}$ alkylthio groups, amide groups with 1 to 4 carbon atoms, $C_{1-4}$ acyl groups and a cyano group. Preferably, $R^5$ is a hydrogen atom, a substituted or unsubstituted $C_{1-4}$ alkyl group, a $C_{2-4}$ unsubstituted alkenyl group, an alkenyl group substituted with $C_{1-4}$ alkoxy groups, and particularly preferably $R^5$ is a hydrogen atom, a methyl group, an ethyl group, a propyl group, an isopropyl group, a butyl group, an isobutyl group, a vinyl group, a 1-methoxyvinyl group and a 1-ethoxyvinyl group.

Particularly preferred examples of monomers for resists which are represented by the formula 1 include, for example, γ-butyrolactone-3-yl(meth)acrylate, mevalonolactone(meth) acrylate, γ-butyrolactone-3-methyl-3-yl(meth)acrylate, γ-butyrolactone-2-yl(meth)acrylate, 1-(γ-butyrolactone-2-yl)ethyl(meth)acrylate, pantolactone(meth)acrylate, γ-butyrolactone-2-methyl-2-yl(meth)acrylate, 1-(γ-butyrolactone-2-yl)propyl(meth)acrylate, γ-butyrolactone-3-ethyl-3-yl (meth)acrylate and γ-butyrolactone-2-ethyl-2-yl(meth) acrylate.

Biocatalysts used in the present invention are not particularly limited, as long as they originate from living organisms and capable of catalyzing the above-described esterification or transesterification, and their types and origins are not restricted. Preferred biocatalysts may originate from microorganisms or from animals and plants, and particularly preferred biocatalysts are generally enzymes having hydrolase activity such as lipase activity, esterase activity, protease activity and amidase activity.

Typical examples of the enzymes which originates from microorganisms are Lipase P (originates from genus *Pseudomonas*) from Amano Enzyme Inc., Lipase PS (originates from *Pseudomonas cepacia*) from Amano Enzyme Inc., Lipase A6 (originates from genus *Aspergillus*) from Amano Enzyme Inc., Lipase AP6 (originates from genus *Aspergillus*) from Amano Enzyme Inc., Lipase M-10 (originates from genus *Mucor*) from Amano Enzyme Inc., Lipase OF (originates from genus *Candida*) from Meito Sangyo Co., Ltd., Lipase PL (originates from genus *Alcaligenes*) from Meito Sangyo Co., Ltd., Lipase QLM (originates from genus *Alcaligenes*) from Meito Sangyo Co., Ltd., Lipase SL (originates from *Burkholderia cepacia*) from Meito Sangyo Co., Ltd., Lipase TL (originates from *Pseudomonas stutzeri*) from Meito Sangyo Co., Ltd., Lipase MY (originates from *Candida cylindracea*) from Meito Sangyo Co., Ltd., Toyozyme LIP (originates from genus *Pseudomonas*) from TOYOBO Co., Ltd., Lipase Type VII (originates from *Candida rugosa*) from Sigma-Aldrich, Inc., Acylase I (originates from *Aspergillus melleus*) from Sigma-Aldrich, Inc., Protease Type XXXI (originates from *Bacillus licheniformis*) from Sigma-Aldrich, Inc., Lipase (originates from *Candida antarctica*) from Fluka, Lipozyme IM 20 (originates from *Humicola lanuginosa*) from Novo Nordisk Pharma Ltd., Lipase M (originates from *Mucor javanicus*) from Amano Enzyme Inc., Lipase MFL from Amano Enzyme Inc., Novozym435 (originates from *Candida antarctica*) from Novo Nordisk Pharma Ltd., Lipozyme RM IM (originates from *Rhizomucor miehei*) from Novo Nordisk Pharma Ltd., Lipozyme TL IM (originates from *Thermomyces lanuginosus*) from Novo Nordisk Pharma Ltd., Alcalase (originates from *Bacillus licheniformis*) from Novo Nordisk Pharma Ltd., Durazym (originates from genus *Bacillus*) from Novo Nordisk Pharma Ltd., Esperase (originates from genus *Bacillus*) from Novo Nordisk Pharma Ltd., Savinase (originates from genus *Bacillus*) from Novo Nordisk Pharma Ltd., Bioplase Conc. (originates from *Bacillus subtilis*) from Nagase Biochemicals Co., Lipase AY (originates from *Candida rugosa*) from Amano Enzyme Inc., Lilipase A-10 (originates from *Rhizopus japonicus*) from Nagase Biochemicals Co., Lipase 2G (originates from genus *Pseudomonas*) from Nagase Biochemicals Co., Bioplase AL-15FG (originates from *Bacillus subtilis*) from Nagase Biochemicals Co., Lipase PS-C "Amano" I (originates from *Pseudomonas cepacia*) from Amano Enzyme Inc., Lipase PS-C "Amano" II (originates from *Pseudomonas cepacia*) from Amano Enzyme Inc., Lipase PS-D "Amano" I (originates from *Pseudomonas cepacia*) from Amano Enzyme Inc., Lipase AK "Amano" 20 (originates from *Pseudomonas fluorescens*) from Amano Enzyme Inc., CHIRAZYME L-2 (originates from *Candida antarctica*) from F. Hoffmann-La Roche Ltd., CHIRAZYME L-3 (originates from *Candida rugosa*) from F. Hoffmann-La Roche Ltd., CHIRAZYME L-3p (originates from *Candida rugosa*) from F. Hoffmann-La Roche Ltd., CHIRAZYME L-6 (originates from genus *Pseudomonas*) from F. Hoffmann-La Roche Ltd., CHIRAZYME L-8 (originates from *Thermomyces lanuginos*) from F. Hoffmann-La Roche Ltd., CHIRAZYME L-9 (originates from genus *Rhizomucor*) from F. Hoffmann-La Roche Ltd., and CHIRAZYME L-10 (originates from genus *Alcaligenes*) from F. Hoffmann-La Roche Ltd.

Typical examples of the enzymes originates from animals are Pancreatin (originates from swine) from Amano Enzyme Inc., Porcine Pancreas Lipase (originates from swine) from Sigma-Aldrich, Inc., CHIRAZYME L-7 (originates from swine) from F. Hoffmann-La Roche Ltd. and typical examples of the same originates from plants include Papain from Sigma-Aldrich, Inc.

Of the above-described enzymes, preferred are Lipase P (originates from genus *Pseudomonas*) from Amano Enzyme Inc., Lipase PS (originates from *Pseudomonas cepacia*) from Amano Enzyme Inc., Lipase PS-C "Amano" I (originates from *Pseudomonas cepacia*) from Amano Enzyme Inc., Lipase PS-C "Amano" II (originates from *Pseudomonas cepacia*) from Amano Enzyme Inc., Lipase PS-D "Amano" I (originates from *Pseudomonas cepacia*) from Amano Enzyme Inc., Lipase AK "Amano" 20 (originates from *Pseudomonas fluorescens*) from Amano Enzyme Inc., Lipase AY (originates from *Candida rugosa*) from Amano Enzyme Inc., Lipase OF (originates from genus *Candida*) from Meito Sangyo Co., Ltd., Lipase PL (originates from genus *Alcaligenes*) from Meito Sangyo Co., Ltd., Lipase QLM (originates from genus *Alcaligenes*) from Meito Sangyo Co., Ltd., Lipase SL (originates from *Burkholderia cepacia*) from Meito Sangyo Co., Ltd., Lipase TL (originates from *Pseudomonas stutzeri*) from Meito Sangyo Co., Ltd., Lipase MY (originates from *Candida cylindracea*) from Meito Sangyo Co. Ltd., Novozym435 (originates from *Candida antarctica*) from Novo Nordisk Pharma Ltd., CHIRAZYME L-2 (originates from *Candida antarctica*) from F. Hoffmann-La Roche Ltd., CHIRAZYME L-6 (originates from genus *Pseudomonas*) from F. Hoffmann-La Roche Ltd., CHIRAZYME L-9 (originates from genus *Rhizomucor*) from F. Hoffmann-La Roche Ltd., and CHIRAZYME L-10 (originates from genus *Alcaligenes*) from F. Hoffmann-La Roche Ltd.

Not only the crude or purified isolated enzymes as described above, but also living cells capable of catalyzing the above-described esterification or transesterification, or the processed product thereof can be used as biocatalysts as they are. As such living cells, microorganisms, animal cells and plant cells can be used. For example, a culture solution obtained by culturing a microorganism can be used as it is, or cell body obtained from the above culture by harvesting process such as centrifugation, or processed product thereof can be used. In cases where synthesized enzymes are secreted extracellularly, culture solutions after cell removal operations, such as centrifugation, can be used as they are. However, it is more effective to subject such culture solutions to concentration process and purification process such as ammonium sulfate treatment. Processed product of cell body includes, for example, cell body treated with acetone or toluene, etc., freeze-dried cell body, disrupted cells, cell-free extract from disrupting cells, and a crude enzyme solution obtained by extracting the enzyme from any one thereof.

Typical examples of the microorganisms used as biocatalysts include, not particularly limited, microorganisms of: genus *Pseudomonas*, genus *Agrobacterium*, genus *Bacillus*, genus *Microbacterium*, genus *Aspergillus*, genus *Mucor*, genus *Rhizomucor*, genus *Mortierella*, genus *Nocardia*, genus *Stenotrophomonas*, genus *Brevundimonas*, genus *Rhodococcus*, genus *Aeromonas*, genus *Candida*, genus *Pichia*, genus *Debaryomyces*, genus *Alcaligenes*, genus *Humicola*, genus *Thermomyces*, and genus *Rhizopus*.

More specifically, microorganisms of genus *Pseudomonas* include, for example, *Pseudomonas cepacia*, *Pseudomonas aeruginosa* (IAM 1220), *Pseudomonas aeruginosa* (IAM 1267), *Pseudomonas aeruginosa* (IAM 1275), *Pseudomonas aeruginosa* (IAM 1514), *Pseudomonas fluorescens* (IAM 1008) and *Pseudomonas ovalis* (IAM 1002); microorganisms of genus *Agrobacterium* include, for example, *Agrobacterium rhizogenes* (IFO 13257); microorganisms of genus *Bacillus* include, for example, *Bacillus subtilis* and *Bacillus licheniformis*; microorganisms of genus *Microbacterium* include, for example, *Microbacterium barkeri* (JCM 1343); microorganisms of genus *Aspergillus* include, for example, *Aspergillus niger*, *Aspergillus melleus* and *Aspergillus oryzae*; microorganisms of genus *Mucor* include, for example, *Mucor miehei* and *Mucor javanicus* (IFO 4572); microorganisms of genus *Mortierella* include, for example, *Mortierella isabellina* (IFO 7824); microorganisms of genus *Nocardia* include, for example, *Nocardia rubra* (IFM 18); microorganisms of genus *Stenotrophomonas* include, for example, *Stenotrophomonas maltophilia* (IFO 12020) and *Stenotrophomonas maltophilia* (IFO 12690); microorganisms of genus *Brevundimonas* include, for example, *Brevundimonas diminuta* (IFO 14213); microorganisms of genus *Rhodococcus* include, for example, *Rhodococcus equi* (IFO 3730); microorganisms of genus *Aeromonas* include, for example, *Aeromonas hydrophila* (IFO 3820); microorganisms of genus *Candida* include, for example, *Candida rugosa*, *Candida antarctica* and *Candida tropicalis* (IAM 4965); microorganisms of genus *Pichia* include, for example, *Pichia anomala* (IFO 146); microorganisms of genus *Debaryomyces* include, for example, *Debaryomyces hansenii* (IFO 34); microorganisms of genus *Humicola* include, for example, *Humicola lanuginose*; microorganisms of genus *Thermomyces* include, for example, *Thermomyces lanuginos*; and microorganisms of genus *Rhizopus* include, for example, *Rhizopus japonicus*. Among the above-described microorganisms, preferred are *Pseudomonas aeruginosa* (IAM 1267), *Pseudomonas aeruginosa* (IAM 1220), *Pseudomonas aeruginosa* (IAM 1514), *Brevundimonas diminuta* (IFO 14213), *Nocardia rubra* (IFM 18) and *Rhodococcus equi* (IFO 3730).

These microorganisms are well known and can be obtained easily from, for example, Institute for Fermentation, Osaka (IFO), Institute of Applied Microbiology, the University of Tokyo (IAM), Japan Collection of Microorganisms, Institute of Physical and Chemical Research (JCM), and Research Center for Pathogenic Fungi and Microbial Toxioses, Chiba university.

The variants of the above-described organisms or microorganisms obtained by isolating the intended enzyme genes, introducing the same into a host vector system in the usual way, and transforming a host with the vector, can also be used.

Microorganisms that catalyze the reaction of the present invention can be obtained by, for example, the following process. First suitable nutrient medium, for example, liquid medium is selected, and microorganisms are cultured in the medium. After completion of the cultivation, cultivated cells and supernatant are harvested by a process such as centrifugation. The cell body or supernatant is added to a solution that contains compounds represented by the general formulae 2 and 3, and the solution is shaken at, for example, 30° C. After completion of the reaction, the presence or absence of the compound represented by the general formula 1 is determined by GC (gas chromatography), thereby determining the presence or absence of activity thereof.

In the process of the present invention, when using biocatalysts in the reaction, the form in which the biocatalysts are used is not particularly limited, as long as they have catalytic activity. The biocatalysts can be used after immobilizing them on appropriate carriers by conventional process. Immobilization can be achieved by encompassing the biocatalyst in, for example, cross-linked acrylamide gel polysaccharides or by immobilizing the biocatalysts physically or chemically on solid carriers such as ion-exchange resin, diatomaceous earth and ceramic. The catalytic activities of biocatalysts are often increased when used in the immobilized form. In addition, the use of biocatalysts in the immobilized state makes easy their separation and recovery after completion of the reaction, thereby the biocatalysts can be recycled and the isolation of reaction products becomes easy.

The water content of these biocatalysts can be reduced by subjecting them to freeze-drying or vacuum drying treatment or to treatment using organic solvents such as acetone, methanol and ethanol. The use of the biocatalysts having been subjected to such treatment often allows the reaction to proceed smoothly.

In the present invention, usually one kind of biocatalyst selected from the above-described ones is used. However, it is also possible to use two or more kinds of biocatalysts of similar activity in the mixed form.

In the present invention, any medium for culturing microorganism, which is one of biocatalyst sources, can be used as long as the microorganism can grow therein. As a carbon source, saccharides such as glucose, sucrose and maltose; organic acids such as acetic acid, citric acid and fumaric acid and the salts thereof; and alcohols such as ethanol and glycerol can be used. As a nitrogen source, not only general types of natural nitrogen sources such as peptone, meat extract, yeast extract and amino acid, but also various kinds of inorganic ammonium salts and organic acid ammonium salts can be used. Besides, inorganic salts, trace metal salts, vitamins, etc. are appropriately added if desired. To obtain higher catalytic activities, it is also effective to culture microorganisms using medium containing olive oil, soy bean oil, etc. or medium containing compounds having an ester bond or an amide bond.

The microorganisms can be cultured by conventional process. For example, the cultivation is carried out under aerobic condition for 6 to 96 hours, at pH 4 to 10, and at temperature of 15 to 40° C.

In the present invention, the esterification or transesterification in the process for producing a monomer for resists represented by the general formula 1 can be carried out in the following manner.

Alcohol represented by the general formula 2 or the ester thereof and a compound represented by the general formula 3, both of which are starting materials, are mixed in the presence of the above-described biocatalysts to be dissolved or suspended. The obtained solution or suspension is reacted while controlling the conditions such as temperature.

Taking into consideration their applications and biocatalytic reaction, it is preferable that the alcohol represented by the general formula 2 or the ester thereof and the compound represented by the general formula 3, as starting materials, are of high purity. Therefore, it is natural to prevent their contamination with impurities and it is much more preferable to remove their impurities. For example, when the alcohol represented by the general formula 2 or the ester thereof includes by-products, inorganic salts, etc. produced during its production process, the above impurities are preferably removed to a level that does not inhibit the biocatalytic reaction. Addition of known compounds with reaction accelerating activity, enables the reaction to progress efficiently.

The use of a reaction solvent is arbitrary, and a reaction solvent may be used if desired. When using a reaction solvent, usually an anhydrous organic solvent is used. However, reaction can be carried out in a system containing an aqueous medium such as ion exchange water and buffer solution. As an organic solvent, alcohol solvents such as methanol, ethanol, propanol, isopropanol, butanol, isobutanol, t-butyl alcohol and t-amyl alcohol; aliphatic hydrocarbon solvents such as pentane, hexane, heptane and octane; aromatic hydrocarbon solvents such as benzene, toluene and xylene; hydrocarbon halide solvents such as methylene chloride, chloroform, carbon tetrachloride and dichloroethane; ether solvents such as diethyl ether, diisopropyl ether, methyl t-butyl ether, tetrahydrofuran and dioxane; ester solvents such as ethyl acetate, propyl acetate and butyl acetate; ketone solvents such as acetone, methyl ethyl ketone and methyl isobutyl ketone; acetontrile; and N,N-dimethylformamide can be appropriately used. Among these solvents, preferred are t-butyl alcohol, hexane, octane, diisopropyl ether and methyl-t-butyl ether. Reaction can be carried out in a two-layer system where an organic solvent selected from those described above is added in an amount beyond its solubility in water.

The molar ratio of two starting materials in the reaction solution, for example, a compound represented by the general formula 2 and a compound represented by the general formula 3 and the concentrations thereof are arbitrary and are not particularly limited. When using a reaction solvent in addition to the above two starting materials, usually the concentrations of the materials are both in the range of 0.1 to 40% by weight based on the weight of the reaction solution. Taking into consideration the productivity, it is preferable to carry out the reaction with the concentrations of both materials kept 0.5% by weight or more. When using no reaction solvent, taking into consideration the post-treatment, it is preferable to use the compound represented by the general formula 3 in excess of alcohol represented by the general formula 2 or the ester thereof. In this case, the compound represented by the general formula 3 is preferably used in an amount 5 to 1000 times as equivalent as the alcohol represent by the general formula 2 or the ester thereof.

The concentration of the biocatalyst in the reaction solution is determined appropriately depending on the form in which the catalyst is used and the conditions under which the reaction is carried out. Usually, it is 0.01 to 50% by weight, preferably 0.05 to 20% by weight base on the weight of the reaction solution.

The other conditions such as reaction temperature and reaction time are determined appropriately depending on the starting materials used and the activity of the biocatalyst, and they are not particularly limited. However, the reaction is usually carried out at 5 to 80° C. for 1 hour to 1 week, preferably at 10 to 70° C. for 1 to 120 hours. Preferably, the conditions are selected so that the reaction completes under the above conditions.

Further, it is preferable from the viewpoint of chemical kinetics that the reaction is carried out while distilling the water, alcohol and aldehyde produced during esterification or transesterification out of the system. Therefore, it is effective to carry out the reaction under reduced pressure. Further, a solvent may be added which forms an azeotropic composition together with the alcohol, water, etc. as a by-product. Examples of such solvents are, not particularly limited, methyl ethyl ketone, methyl isopropyl ketone, methyl isobutyl ketone, n-hexane and n-heptane.

Preferably the reaction conditions, such as conditions for preparing starting material, biocatalyst concentration, temperature, solvent, pH and reaction time, are appropriately selected, taking into consideration the reaction yield under such conditions, so that the intended monomer can be obtained in the maximum amount.

In some cases, some monomers among those represented by the general formula 1 have an asymmetric carbon atom in the alcohol portion. However, it does not matter which one of R- and S-configurations of antipode or racemic body reacts. A monomer having any configuration can be produced, by selecting an appropriate biocatalyst, depending on the purpose or use thereof.

The monomer produced can be isolated from the reaction solution by the known isolating process such as distillation, thin film distillation, extraction washing or column separation.

For example, the intended monomer can be isolated through following procedure: removing the biocatalyst by filtration etc.; distilling the reaction solvent or the unreacted subject out of the reacted solution; and evaporating or column-purifying the solution.

This specification encompasses the contents described in the specification and/or drawings of Japanese Patent Application No. 2001-277210 which the priority of this application is based on.

BEST MODE FOR CARRYING OUT THE INVENTION

In the following the present invention will be described in further detail giving several examples; however, it should be understood that the scope of the invention is not intended to be limited to the examples.

EXAMPLE 1

Synthesis of γ-butyrolactone-3-ylmethacrylate

β-hydroxy-γ-butyrolactone and vinylmethacrylate were dissolved in 3 ml of t-butanol (t-BuOH) in concentrations of 1.0% (W/V) and 1.1% (W/V), respectively. Each enzyme shown in Table 1 was added to the solution in concentration of about 1 to 5% (W/V) and reacted for 24 hours at 30° C. The amount of γ-butyrolactone-3-ylmethacrylate in each solution after completion of the reaction was determined by gas chromatography (column; TC-1701 (0.25 mm×30 m from GL Sciences Inc.)) and the yield was calculated. The results are shown in Table 1.

The optical purity (enantiomer excess; % e.e.) of the synthesized γ-butyrolactone-3-ylmethacrylate was analyzed for some of the mixed solutions using an optical resolution GC capillary column (Chirasil-DEX CB column from Chrompack, B.V.).

TABLE 1

| Enzyme | Product Concentration % | Yield % | Optical Purity |
|---|---|---|---|
| Lipase P from Amano Enzyme | 1.276 | 84.53% | NT |
| Lipase PS from Amano Enzyme | 0.326 | 21.62% | (S) 52% ee |
| Lipase A6 from Amano Enzyme | 0.008 | 0.52% | NT |
| Lipase AP6 from Amano Enzyme | 0.008 | 0.55% | NT |
| Lipase M-10 from Amano Enzyme | 0.012 | 0.82% | NT |
| Lipase OF from Meito Sangyo | 0.293 | 19.38% | (S) 21% ee |
| Toyozyme LIP from TOYOBO | 0.185 | 12.24% | (S) 19% ee |
| Lipase Type VII from SIGMA | 0.039 | 2.58% | NT |
| Porcine Pancreas Lipase from SIGMA | 0.011 | 0.76% | NT |
| Acylase I from SIGMA | 0.023 | 1.50% | NT |
| Papain from SIGMA | 0.018 | 1.21% | (R) 6% ee |
| Protease Type XXXI from SIGMA | 0.053 | 3.53% | (S) 7% ee |
| Lipase from Fluka | 0.080 | 5.31% | NT |
| Lipozyme IM 20 from NOVO | 0.032 | 2.15% | (R) 7% ee |
| Lipase M from Amano Enzyme | 0.048 | 3.20% | NT |
| Lipase MFL from Amano Enzyme | 0.008 | 0.56% | NT |
| Alcalase from NOVO | 0.085 | 5.62% | NT |
| Durazym from NOVO | 0.054 | 3.58% | NT |
| Esperase from NOVO | 0.009 | 0.60% | NT |
| Savinase from NOVO | 0.040 | 2.67% | NT |
| Bioplase Conc. from Nagase Biochemicals | 0.038 | 2.53% | NT |
| Lipase AY from Amano Enzyme | 0.054 | 3.58% | (S) 40% ee |
| Lilipase A-10 from Nagase Biochemicals | 0.062 | 4.11% | (S) 35% ee |
| Lipase 2G from Nagase Biochemicals | 0.038 | 2.52% | NT |
| Bioplase AL-15FG from Nagase Biochemicals | 0.064 | 4.22% | (R) 7% ee |
| Lipase PS-C "Amano" II from Amano Enzyme | 1.401 | 92.80% | (S) 15% ee |
| Lipase PS-D "Amano" I from Amano Enzyme | 1.004 | 66.52% | (S) 33% ee |
| Lipase AK "Amano" 20 from Amano Enzyme | 0.901 | 59.67% | NT |
| Lipase PS-C "Amano" I from Amano Enzyme | 0.708 | 46.91% | NT |
| CHIRAZYME L-2 from Roche | 0.419 | 27.76% | NT |
| CHIRAZYME L-3 from Roche | 0.017 | 1.15% | NT |
| CHIRAZYME L-3p from Roche | 0.027 | 1.82% | NT |
| CHIRAZYME L-6 from Roche | 0.678 | 44.87% | NT |
| CHIRAZYME L-7 from Roche | 0.032 | 2.12% | NT |
| CHIRAZYME L-8 from Roche | 0.002 | 0.16% | NT |
| CHIRAZYME L-9 from Roche | 0.251 | 16.63% | NT |
| CHIRAZYME L-10 from Roche | 0.919 | 60.83% | NT |
| Lipase PL from Meito Sangyo | 0.926 | 61.32% | NT |
| Lipase QLM from Meito Sangyo | 0.901 | 59.67% | NT |
| Lipase SL from Meito Sangyo | 0.436 | 28.87% | NT |
| Lipase TL from Meito Sangyo | 0.563 | 37.28% | NT |
| Lipase MY from Meito Sangyo | 0.397 | 26.29% | NT |
| Lipozyme RM IM from NOVO | 0.109 | 7.22% | NT |
| Lipozyme TL IM from NOVO | 0.224 | 14.83% | NT |

NT; not tested

EXAMPLE 2

Synthesis of γ-butyrolactone-3-ylmethacrylate

β-hydroxy-γ-butyrolactone was dissolved in 3 ml of methylmethacrylate (MMA) in concentration of 1.0% (W/V). Each enzyme shown in Table 2 was added to the solution in concentration of about 1 to 5% (W/V) and incubated for 24 hours at 30° C. The analysis was conducted in the same manner as example 1. The results are shown in Table 2.

TABLE 2

| Enzyme | Product Concentration % | Yield % | Optical Purity |
|---|---|---|---|
| Lipase P from Amano Enzyme | 0.085 | 5.66% | (S) 50% ee |
| Lipase PS from Amano Enzyme | 0.024 | 1.59% | (S) 49% ee |
| Pancreatin from Amano Enzyme | 0.009 | 0.60% | (S) 35% ee |
| Lipase OF from Meito Sangyo | 0.161 | 10.66% | (S) 60% ee |
| Toyozyme LIP from TOYOBO | 0.095 | 6.31% | (S) 25% ee |
| Lipase Type VII from SIGMA | 0.184 | 12.20% | (S) 64% ee |
| Lipase from Fluka | 0.071 | 4.72% | (S) 45% ee |
| Lipozyme IM 20 from NOVO | 0.010 | 0.64% | (S) 56% ee |
| Lipase MFL from Amano Enzyme | 0.016 | 1.09% | (S) 60% ee |
| Esperase from NOVO | 0.007 | 0.48% | (R) 28% ee |
| Lipase AY from Amano Enzyme | 0.203 | 13.41% | (S) 59% ee |
| Lipase 2G from Nagase Biochemicals | 0.030 | 1.96% | (R) 13% ee |
| Lipase PS-C "Amano" II from Amano Enzyme | 0.612 | 40.52% | (S) 17% ee |
| Lipase PS-D "Amano" I from Amano Enzyme | 0.235 | 15.54% | (S) 45% ee |
| Lipase AK "Amano" 20 from Amano Enzyme | 0.164 | 10.84% | (S) 52% ee |
| Lipase PS-C "Amano" I from Amano Enzyme | 0.622 | 41.20% | (S) 22% ee |
| CHIRAZYME L-2 from Roche | 0.701 | 46.44% | NT |
| CHIRAZYME L-6 from Roche | 0.005 | 0.35% | NT |
| CHIRAZYME L-7 from Roche | 0.005 | 0.32% | NT |
| CHIRAZYME L-9 from Roche | 0.006 | 0.37% | NT |
| CHIRAZYME L-10 from Roche | 0.235 | 15.56% | NT |

NT; not test

EXAMPLE 3

Synthesis of γ-butyrolactone-3-ylmethacrylate

β-hydroxy-γ-butyrolactone was dissolved in 3 ml of n-butylmethacrylate in concentration of 1.0% (W/V). Each enzyme shown in Table 3 was added to the solution in concentration of about 1 to 5% (W/V) and incubated for 24 hours at 30° C. The analysis was conducted in the same manner as example 1. The results are shown in Table 3.

TABLE 3

| Enzyme | Product Concentration % | Yield % |
|---|---|---|
| Lipase P from Amano Enzyme | 0.306 | 20.27% |
| Lipase PS from Amano Enzyme | 0.114 | 7.55% |
| Pancreatin from Amano Enzyme | 0.019 | 1.27% |
| Lipase OF from Meito Sangyo | 0.587 | 38.86% |
| Toyozyme LIP from TOYOBO | 0.694 | 45.99% |
| Lipase Type VII from SIGMA | 0.457 | 30.28% |
| Lipase from Fluka | 0.078 | 5.20% |
| Lipozyme IM 20 from NOVO | 0.062 | 4.13% |
| Lipase MFL from Amano Enzyme | 0.009 | 0.61% |
| Lipase AY from Amano Enzyme | 0.311 | 20.61% |
| Lipase 2G from Nagase Biochemicals | 0.033 | 2.16% |
| Lipase PS-C "Amano" II from Amano Enzyme | 0.858 | 56.80% |
| Lipase PS-D "Amano" I from Amano Enzyme | 0.659 | 43.64% |
| Lipase AK "Amano" 20 from Amano Enzyme | 0.066 | 4.38% |
| Lipase PS-C "Amano" I from Amano Enzyme | 0.582 | 38.53% |

EXAMPLE 4

Synthesis of 1-(γ-butyrolactone-2-yl)ethylmethacrylate

α-(1-hydroxyethyl)-γ-butyrolactone and vinylmethacrylate were dissolved in 3 ml of t-BuOH in concentrations of 1.0% (W/V) and 0.87% (W/V), respectively. Each enzyme shown in Table 4 were added to the solution in concentration of about 1 to 5% (W/V) and incubated for 24 hours at 30° C. The analysis was conducted in the same manner as example 1, and the amount of 1-(γ-butyrolactone-2-yl)ethylmethacrylate in the solution after completion of the incubation was determined. The results are shown in Table 4.

TABLE 4

| Enzyme | Product Concentration % |
|---|---|
| Lipase OF from Meito Sangyo | 0.069 |
| Toyozyme LIP from TOYOBO | 0.430 |
| Lipase Type VII from SIGMA | 0.011 |
| Bioplase Conc. From Nagase Biochemicals | 0.007 |
| Lipase AY from Amano Enzyme | 0.023 |
| Lipase 2G from Nagase Biochemicals | 0.014 |
| Bioplase AL-15FG from Nagase Biochemicals | 0.007 |
| Lipase PS-C "Amano" II from Amano Enzyme | 0.518 |

EXAMPLE 5

Synthesis of Pantolactone Methacrylate

Pantolactone and vinylmethacrylate were dissolved in 3 ml of t-BuOH in concentrations of 1.0% (W/V) and 0.87% (W/V), respectively. Each enzyme shown in Table 5 was added to the solution in concentration of about 1 to 5% (W/V) and incubated for 24 hours at 30° C. The analysis was conducted in the same manner as example 1, and the amount of pantolactone methacrylate in the solution after the incubation was determined. The results are shown in Table 5.

TABLE 5

| Enzyme | Product Concentration % |
|---|---|
| Lipase OF from Meito Sangyo | 0.091 |
| Toyozyme LIP from TOYOBO | 0.013 |
| Protease Type XXXI from SIGMA | 0.008 |
| Lipase from Fluka | 0.005 |
| Bioplase Conc. From Nagase Biochemicals | 0.007 |
| Bioplase AL-15FG from Nagase Biochemicals | 0.011 |
| Lipase PS-C "Amano" II from Amano Enzyme | 0.045 |

REFERENTIAL EXAMPLE

Preparation of Acetone-treated Cells

Microorganisms shown in Table 6 were incubated for 48 to 72 hours at 30° C. in the medium described below. Five ml of the culture was taken, and the cells were harvested by centrifugation and washed sequentially with the same amount of 50 mM phosphate buffer ($K_2HPO_4/KH_2PO_4$ buffer, pH 7.0) twice and then with the same amount of acetone 3 times. The acetone-treated cells were dried for 1 hour at room temperature under reduced pressure.

| Composition of Medium | |
|---|---|
| Glucose | 20 g |
| Peptone | 5 g |
| NaCl | 5 g |
| Yeast Extract | 5 g |
| $KH_2PO_4$ | 5 g |
| Distilled Water | 1 L |
| | pH 7.0 |

After autoclaving the medium, methyl lactate and butyl acetate were added aseptically to the medium in concentrations of in the medium each were 0.04% (W/V).

EXAMPLE 6

Synthesis of γ-butyrolactone-3-ylmethacrylate

β-hydroxy-γ-butyrolactone and vinylmethacrylate were dissolved in 1 ml of t-BuOH in concentrations of 1.0% (W/V) and 1.1% (W/V), respectively. Each kind of acetone-treated cells obtained in referential example was added to the solution in concentration of 3% (W/V) and incubated for 24 hours at 30° C. The analysis was conducted in the same manner as example 1. The results are shown in Table 6.

TABLE 6

| Name of Microorganisms | | Product Concentration % | Yield % |
|---|---|---|---|
| Agrobacterium rhizogenes | IFO 13257 | 0.005 | 0.30% |
| Microbacterium barkeri | JCM 1343 | 0.004 | 0.25% |
| Mucor javanicus | IFO 4572 | 0.003 | 0.19% |
| Mortierella isabellina | IFO 7824 | 0.005 | 0.35% |
| Nocardia rubra | IFM 18 | 0.003 | 0.18% |
| Pseudomonas aeruginosa | IAM 1220 | 0.009 | 0.61% |
| Pseudomonas aeruginosa | IAM 1267 | 0.042 | 2.81% |
| Pseudomonas aeruginosa | IAM 1275 | 0.003 | 0.23% |
| Pseudomonas aeruginosa | IAM 1514 | 0.012 | 0.80% |
| Pseudomonas fluorescens | IAM 1008 | 0.002 | 0.16% |
| Pseudomonas ovalis | IAM 1002 | 0.004 | 0.24% |
| Stenotrophomonas maltophilia | IFO 12020 | 0.010 | 0.68% |
| Stenotrophomonas maltophilia | IFO 12690 | 0.010 | 0.64% |
| Brevundimonas diminuta | IFO 14213 | 0.011 | 0.71% |
| Rhodococcus equi | IFO 3730 | 0.006 | 0.43% |
| Aeromonas hydrophila | IFO 3820 | 0.003 | 0.18% |
| Candida tropicalis | IAM 4965 | 0.005 | 0.31% |
| Pichia anomala | IFO 146 | 0.003 | 0.23% |
| Debaryomyces hansenii | IFO 34 | 0.004 | 0.24% |

EXAMPLE 7

Synthesis of γ-butyrolactone-3-ylmethacrylate

β-hydroxy-γ-butyrolactone was dissolved in 1 ml of MMA in concentration of 1.0% (W/V). Each kind of acetone-treated cell bodies of the microorganisms shown in Table 7 was added to the solution in concentration of 3% (W/V) and incubated for 48 hours at 30° C. The analysis was conducted in the same manner as example 1. The results are shown in Table 7.

TABLE 7

| Name of Microorganisms | | Product Concentration % | Yield % |
|---|---|---|---|
| Agrobacterium rhizogenes | IFO 13257 | 0.003 | 0.17% |
| Nocardia rubra | IFM 18 | 0.029 | 1.94% |
| Pseudomonas aeruginosa | IAM 1220 | 0.011 | 0.70% |
| Pseudomonas aeruginosa | IAM 1267 | 0.039 | 2.59% |
| Pseudomonas aeruginosa | IAM 1275 | 0.009 | 0.62% |
| Pseudomonas aeruginosa | IAM 1514 | 0.022 | 1.48% |
| Pseudomonas fluorescens | IAM 1008 | 0.004 | 0.28% |
| Stenotrophomonas maltophilia | IFO 12020 | 0.010 | 0.68% |
| Brevundimonas diminuta | IFO 14213 | 0.028 | 1.87% |
| Rhodococcus equi | IFO 3730 | 0.028 | 1.83% |

EXAMPLE 8

Synthesis of γ-butyrolactone-3-ylmethacrylate

β-hydroxy-γ-butyrolactone and vinylmethacrylate were dissolved in 10 ml of solvents shown in Table 8 in concentrations of 10% (W/V) and 11% (W/V), respectively. Lipase PS-D "AMANO" I from Amano Enzyme Inc. was added to the solutions in concentration of 10% (W/V) and incubated for 24 hours at 50° C. The analysis was conducted in the same manner as example 1. The results are shown in Table 8.

TABLE 8

| Reaction Solvent | Product Concentration % |
|---|---|
| methyl ethyl ketone | 99% |
| 1,4-dioxane | 98% |
| tetrahydrofuran | 97% |
| t-butanol | 97% |
| acetonitrile | 96% |
| Acetone | 96% |
| Pyridine | 18% |

EXAMPLE 9

Synthesis of γ-butyrolactone-3-ylmethacrylate

β-hydroxy-γ-butyrolactone and vinylmethacrylate were dissolved in 10 ml of methylmethacrylate (MMA) in concentrations of 10% (W/V) and 11% (W/V), respectively. Lipase PS-D "Amano" I from Amano Enzyme Inc. was added to the solution in concentration of 10% (W/V) and incubated for 24 hours at 50° C. The analysis was conducted in the same manner as example 1 and proved that γ-butyrolactone-3-ylmethacrylate was produced in a 98% yield.

The solution after completion of the incubation was filtered to remove Lipase PS-D. The filtrate was washed with the same amount of water twice and MAA was distilled out under reduced pressure. γ-butyrolactone-3-ylmethacrylate was obtained in a substantial yield of 94%. The product was analyzed by GC, and GC area percentage was 94.1%.

When the enzyme, Lipase PS-D "AMANO" I removed by the filtration was used in enzymatic reaction under the same conditions as above in the same manner, γ-butyrolactone-3-ylmethacrylate was produced in a 97% yield.

EXAMPLE 10

Synthesis of γ-butyrolactone-3-ylmethacrylate

β-hydroxy-γ-butyrolactone and vinylmethacrylate were dissolved in 10 ml of methylmethacrylate (MMA) in concentrations of 10% (W/V) and 11% (W/V), respectively. Novozym 435 from Novo Nordisk Pharma Ltd. was added to the solutions in concentration of 5% (W/V) and incubated for 24 hours at 50° C. The analysis was conducted in the same manner as example 1 and proved that γ-butyrolactone-3-ylmethacrylate was produced in a 98% yield.

EXAMPLE 11

Synthesis of γ-butyrolactone-3-ylmethacrylate

β-hydroxy-γ-butyrolactone was dissolved in 10 ml of MMA in concentration of 5.0% (W/V). Novozym 435 from Novo Nordisk Pharma Ltd. was added to the solution in concentration of 10% (W/V) and incubated under reduced pressure (250 mmHg) for 24 hours at 50° C. The analysis was conducted in the same manner as example 1 and proved that γ-butyrolactone-3-ylmethacrylate was produced in a 83% yield.

EXAMPLE 12

Synthesis of γ-butyrolactone-3-ylmethacrylate

β-hydroxy-γ-butyrolactone was dissolved in 10 ml of MMA in concentration of 5.0% (W/V). Lipase PS-D "AMANO" I from Amano Enzyme Inc. was added to the solution in concentration of 10% (W/V) and incubated under reduced pressure (250 mmHg) for 24 hours at 50° C. The analysis was conducted in the same manner as example 1 and proved that γ-butyrolactone-3-ylmethacrylate was produced in a 61% yield.

EXAMPLE 13

Synthesis of γ-butyrolactone-3-ylmethacrylate

β-hydroxy-γ-butyrolactone and vinylmethacrylate were dissolved in 10 ml of methylmethacrylate (MMA) in concentrations of 14% (W/V) and 16.5% (W/V), respectively. Lipase PS-D "AMANO" I from Amano Enzyme Inc. was added to the solution in concentration of 10% (W/V) and incubated for 17 hours at 50° C. The analysis was conducted in the same manner as example 1 and proved that γ-butyrolactone-3-ylmethacrylate was produced in a 99% yield.

The entire disclosure of the publications, patents and patent applications cited in this specification is incorporated herein by reference.

INDUSTRIAL APPLICABILITY

According to the process of the present invention, an alicyclic monomer for resists that is bulky and is subject to decomposition by acid can be synthesized without using acid catalysts, under mild conditions, and in such a manner as to make the product purification easier.

The invention claimed is:

1. A process for producing a monomer represented by the following general formula 1,

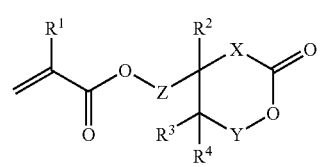

(1)

wherein $R^1$ represents hydrogen or optionally substituted alkyl; $R^2$, $R^3$ and $R^4$ each independently represent hydrogen or a substituent; X and Y each independently represent a direct bond or optionally substituted alkylene with 1 to 3 chain members, and Z represents a direct bond or substituted alkylene with 1 chain member, comprising carrying out esterification or transesterification between a compound represented by the following general formula 2:

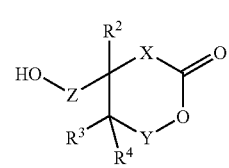

(2)

wherein $R^2$, $R^3$, $R^4$, X, Y and Z are defined as described above for general formula 1, and a compound represented by the following general formula 3:

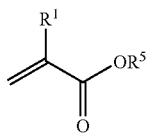

wherein $R^1$ is defined as described above for general formula 1 and $R^5$ represents hydrogen or a substituent, in the presence of a biocatalyst.

2. A process for producing a monomer for resists represented by the following general formula 1:

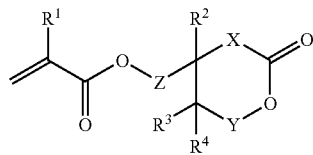

wherein $R^1$ represents hydrogen or optionally substituted alkyl; $R^2$, $R^3$ and $R^4$ each independently represent hydrogen or a substituent; and X, Y and Z each independently represent a direct bond or optionally substituted alkylene with 1 to 3 chain members, comprising carrying out esterification or transesterification between a compound represented by the following general formula 2:

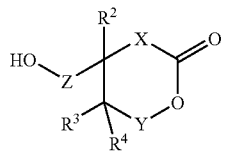

wherein $R^2$, $R^3$, $R^4$, X, Y and Z are defined as described above for general formula 1 provided that a compound wherein OH in formula 2 is linked to a primary carbon atom is excluded, and a compound represented by the following general formula 3:

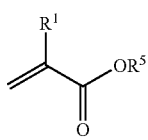

wherein $R^1$ is defined as described above for general formula 1 and $R^5$ represents hydrogen or a substituent, in the presence of a biocatalyst.

3. A process for producing a monomer represented by the following general formula 1,

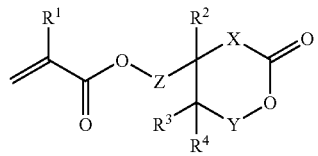

wherein $R^1$ represents hydrogen or optionally substituted alkyl; $R^2$, $R^3$ and $R^4$ each independently represent hydrogen or a substituent; and X, Y and Z each independently represent a direct bond or optionally substituted alkylene with 1 to 3 chain members, comprising carrying out esterification or transesterification between a compound represented by the following general formula 2:

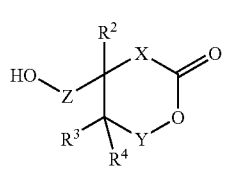

wherein $R^2$, $R^3$, $R^4$, X, Y and Z are defined as described above for general formula 1, and a compound represented by the following general formula 3:

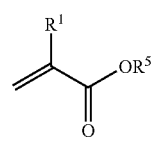

wherein $R^1$ is defined as described above for general formula 1 and $R^5$ represents hydrogen or a substituent, in the presence of a biocatalyst.

4. The process for producing a monomer as claimed in claim 3, wherein said monomer is selected from the group consisting of γ-butyrolactone-3-yl(meth)acrylate, mevalonolactone(meth)acrylate, γ-butyrolactone-3-methyl-3-yl(meth)acrylate, γ-butyrolactone-2-yl(meth)acrylate, 1-(γ-butyrolactone-2-yl)ethyl(meth)acrylate, pantolactone(meth)acrylate, γ-butyrolactone-2-methyl-2-yl(meth)acrylate, 1-(γ-butyrolactone-2-yl)propyl(meth)acrylate, γ-butyrolactone-3-ethyl-3-yl(meth)acrylate and γ-butyrolactone-2-ethyl-2-yl(meth)acrylate.

5. The process for producing a monomer as claimed in claim 1, wherein said monomer is selected from the group consisting of γ-butyrolactone-3-yl(meth)acrylate, mevalonolactone(meth)acrylate, γ-butyrolactone-3-methyl-3-yl(meth)acrylate, γ-butyrolactone-2-yl(meth)acrylate, 1-(γ-butyrolactone-2-yl)ethyl(meth)acrylate, pantolactone(meth)acrylate, γ-butyrolactone-2-methyl-2-yl(meth)acrylate, 1-(γ-butyrolactone-2-yl)propyl(meth)acrylate, γ-butyrolactone-3-ethyl-3-yl(meth)acrylate and γ-butyrolactone-2-ethyl-2-yl(meth)acrylate.

6. The process for producing a monomer as claimed in claim 2, wherein said monomer is selected from the group consisting of γ-butyrolactone-3-yl(meth)acrylate, mevalonolactone(meth)acrylate, γ-butyrolactone-3-methyl-3-yl(meth)acrylate, γ-butyrolactone-2-yl(meth)acrylate, 1-(γ-butyrolactone-2-yl)ethyl(meth)acrylate, pantolactone(meth)acrylate, γ-butyrolactone-2-methyl-2-yl(meth)acrylate, 1-(γ-butyrolactone-2-yl)propyl(meth)acrylate, γ-butyrolactone-3-ethyl-3-yl(meth)acrylate and γ-butyrolactone-2-ethyl-2-yl(meth)acrylate.

7. The process as claimed in claim 1, wherein said biocatalyst comprises at least one enzyme selected from the following group:
Lipase P, Lipase PS, Lipase A6, Lipase AP6, Lipase M-10, Lipase OF, Lipase PL, Lipase QLM, Lipase SL, Lipase TL, Lipase MY, Toyozyme LIP, Lipase Type VII, Acylase I, Protease Type XXXI, Lipase, Lipozyme IM 20, Lipase M, Lipase MFL, Novozym435, Lipozyme RM IM, Lipozyme TL IM, Alcalase, Durazym, Esperase, Savinase, Bioplase Conc., Lipase AY, Lilipase A-10, Lipase 2G, Bioplase AL-15FG, Lipase PS-C "Amano" I, Lipase PS-C "Amano" II, Lipase PS-D "Amano" I, Lipase AK "Amano" 20, CHIRAZYME L-2, CHIRAZYME L-3, CHIRAZYME L-3p, CHIRAZYME L-6, CHIRAZYME L-8, CHIRAZYME L-9, CHIRAZYME L-10, Pancreatin, Porcine Pancreas Lipase, CHIRAZYME L-7, and Papain.

8. The process as claimed in claim 2, wherein said biocatalyst comprises at least one enzyme selected from the following group:
Lipase P, Lipase PS, Lipase A6, Lipase AP6, Lipase M-10, Lipase OF, Lipase PL, Lipase QLM, Lipase SL, Lipase TL, Lipase MY, Toyozyme LIP, Lipase Type VII, Acylase I, Protease Type XXXI, Lipase, Lipozyme TM 20, Lipase M, Lipase MFL, Novozym435, Lipozyme RM IM, Lipozyme TL TM, Alcalase, Durazym, Esperase, Savinase, Bioplase Couc., Lipase AY, Lilipase A-10, Lipase 2G, Bioplase AL-15FG, Lipase PS-C "Amano" I, Lipase PS-C "Amano" II, Lipase PS-D "Amano" I, Lipase AK "Amano" 20, CHIRAZYME L-2, CHIRAZYME L-3, CHIRAZYME L-3p, CHIRAZYME L-6, CHIRAZYME L-8, CHIRAZYME L-9, CHIRAZYME L-10, Pancreatin, Porcine Pancreas Lipase, CHIRAZYME L-7, and Papain.

9. The process as claimed in claim 3, wherein said biocatalyst comprises at least one enzyme selected from the following group:
Lipase P, Lipase PS, Lipase A6, Lipase AP6, Lipase M-10, Lipase OF, Lipase PL, Lipase QLM, Lipase SL, Lipase TL, Lipase MY, Toyozyme LIP, Lipase Type VII, Acylase I, Protease Type XXXI, Lipase, Lipozyme IM 20, Lipase M, Lipase MFL, Novozym435, Lipozyme RM TM, Lipozyme TL TM, Alcalase, Durazym, Esperase, Savinase, Bioplase Conc., Lipase AY, Lilipase A-10, Lipase 2G, Bioplase AL-15FG, Lipase PS-C "Amano" I, Lipase PS-C "Amano" II, Lipase PS-D "Amano" I, Lipase AK "Amano" 20, CHIRAZYME L-2, CHIRAZYME L-3, CHIRAZYME L-3p, CHIRAZYME L-6, CHIRAZYME L-8, CHIRAZYME L-9, CHIRAZYME L-10, Pancreatin, Porcine Pancreas Lipase, CHIRAZYME L-7, and Papain.

10. The process as claimed in claim 1, wherein said biocatalyst comprises at least one microorganism selected from microorganisms of: genus *Pseudomonas*, genus *Agrobacterium*, genus *Bacillus*, genus *Microbacterium*, genus *Aspergillus*, genus *Mucor*, genus *Rhizomucor*, genus *Mortierella*, genus *Nocardia*, genus *Stenotrophomonas*, genus *Brevundimonas*, genus *Rhodococcus*, genus *Aeromonas*, genus *Candida*, genus *Pichia*, genus *Debaryomyces*, genus *Alcaligenes*, genus *Humicola*, genus *Thermomyces*, and genus *Rhizopus*.

11. The process as claimed in claim 2, wherein said biocatalyst comprises at east one microorganism selected from microorganisms of: genus *Pseudomonas*, genus *Agrobacterium*, genus *Bacillus*, genus *Microbacterium*, genus *Aspergillus*, genus *Mucor*, genus *Rhizomucor*, genus *Mortierella*, genus *Nocardia*, genus *Stenotrophomonas*, genus *Brevundimonas*, genus *Rhodococcus*, genus *Aeromonas*, genus *Candida*, genus *Pichia*, genus *Debaryomyces*, genus *Alcaligenes*, genus *Humicola*, genus *Thermomyces*, and genus *Rhizopus*.

12. The process as claimed in claim 3, wherein said biocatalyst comprises at least one microorganism selected from microorganisms of: genus *Pseudomonas*, genus *Agrobacterium*, genus *Bacillus*, genus *Microbacterium*, genus *Aspergillus*, genus *Mucor*, genus *Rhizomucor*, genus *Mortierella*, genus *Nocardia*, genus *Stenotrophomonas*, genus *Brevundimonas*, genus *Rhodococcus*, genus *Aeromonas*, genus *Candida*, genus *Pichia*, genus *Debaryomyces*, genus *Alcaligenes*, genus *Humicola*, genus *Thermomyces*, and genus *Rhizopus*.

13. The process as claimed in claim 1, wherein said biocatalyst comprises at least one microorganism selected from microorganisms of: *Pseudomonas cepacia*, *Pseudomonas aeruginosa* (IAM 1220), *Pseudomonas aeruginosa* (IAM 1267), *Pseudomonas aeruginosa* (IAM 1275), *Pseudomonas aeruginosa* (IAM 1514), *Pseudomonas fluorescens* (IAM 1008), *Pseudomonas ovalis* (IAM 1002), *Agrobacterium rhizogenes* (IFO 13257), *Bacillus subtilis*, *Bacillus licheniformis*, *Microbacterium barkeri* (JCM 1343), *Aspergillus niger*, *Aspergillus melleus*, *Aspergillus oryzae*, *Mucor miehei*, *Mucor javanicus* (IFO 4572), *Mortierella isabellina* (IFO 7824), *Nocardia rubra* (IFM 18), *Stenotrophomonas maltophilia* (IFO 12020), *Stenotrophomonas maltophilia* (IFO 12690), *Brevundimonas diminuta* (IFO 14213), *Rhodococcus equi* (IFO 3730, *Aeromonas hydrophila* (IFO 3820), *Candida rugosa*, *Candida antarctica*, *Candida tropicalis* (IAM 4965), *Pichia anomala* (IFO 146), *Debaryomyces hansenii* (IFO 34), *Humicola lanuginose*, *Thermomyces lanuginos*, and *Rhizopus japonicus*.

14. The process as claimed in claim 2, wherein said biocatalyst comprises at least one microorganism selected from microorganisms of: *Pseudomonas cepacia*, *Pseudomonas aeruginosa* (IAM 1220), *Pseudomonas aeruginosa* (IAM 1267), *Pseudomonas aeruginosa* (IAM 1275), *Pseudomonas aeruginosa* (IAM 1514), *Pseudomonas fluorescens* (IAM 1008), *Pseudomonas ovalis* (IAM 1002), *Agrobacterium rhizogenes* (IFO 13257), *Bacillus subtilis*, *Bacillus licheniformis*, *Microbacterium barkeri* (JCM 1343), *Aspergillus niger*, *Aspergillus melleus*, *Aspergillus oryzae*, *Mucor miehei*, *Mucor javanicus* (IFO 4572), *Mortierella isabellina* (IFO 7824), *Nocardia rubra* (IFM 18), *Stenotrophomonas maltophilia* (IFO 12020), *Stenotrophomonas maltophilia* (IFO 12690), *Brevundimonas diminuta* (IFO 14213), *Rhodococcus equi* (IFO 3730, *Aeromonas hydrophila* (IFO 3820), *Candida rugosa*, *Candida antarctica*, *Candida tropicalis* (IAM 4965), *Pichia anomala* (IFO 146), *Debaryomyces hansenii* (IFO 34), *Humicola lanuginose*, *Thermomyces lanuginos*, and *Rhizopus japonicus*.

15. The process as claimed in claim 3, wherein said biocatalyst comprises at least one microorganism selected from microorganisms of: *Pseudomonas cepacia*, *Pseudomonas aeruginosa* (IAM 1220), *Pseudomonas aeruginosa* (IAM 1267), *Pseudomonas aeruginosa* (IAM 1275),

*Pseudomonas aeruginosa* (IAM 1514), *Pseudomonas fluorescens* (IAM 1008), *Pseudomonas ovalis* (IAM 1002), *Agrobacterium rhizogenes* (IFO 13257), *Bacillus subtilis, Bacillus licheniformis, Microbacterium barkeri* (JCM 1343), *Aspergillus niger, Aspergillus melleus, Aspergillus oryzae, Mucor miehei, Mucor javanicus* (IFO 4572), *Mortierella isabellina* (IFO 7824), *Nocardia rubra* (IFM 18), *Stenotrophomonas maltophilia* (IFO 12020), *Stenotrophomonas maltophilia* (IFO 12690), *Brevundimonas diminuta* (IFO 14213), *Rhodococcus equi* (IFO 3730, *Aeromonas hydrophila* (IFO 3820), *Candida rugosa, Candida antarctica, Candida tropicalis* (IAM 4965), *Pichia anomala* (IFO 146), *Debaryomyces hansenii* (IFO 34), *Humicola lanuginose, Thermomyces lanuginos*, and *Rhizopus japonicus*.

16. The process as claimed in claim 1, wherein said biocatalyst comprises at least one microorganism selected from microorganisms of: *Pseudomonas aeruginosa* (IAM 1267), *Pseudomonas aeruginosa* (IAM 1220), *Pseudomonas aeruginosa* (IAM 1514), *Brevundimonas diminuta* (IFO 14213), *Nocardia rubra* (IFM 18) and *Rhodococcus equi* (IFO 3730).

17. The process as claimed in claim 2, wherein said biocatalyst comprises at least one microorganism selected from microorganisms of: *Pseudomonas aeruginosa* (IAM 1267), *Pseudomonas aeruginosa* (IAM 1220), *Pseudomonas aeruginosa* (IAM 1514), *Brevundimonas diminuta* (IFO 14213), *Nocardia rubra* (IFM 18) and *Rhodococcus equi* (IFO 3730).

18. The process as claimed in claim 3, wherein said biocatalyst comprises at least one microorganism selected from microorganisms of: *Pseudomonas aeruginosa* (IAM 1267), *Pseudomonas aeruginosa* (IAM 1220), *Pseudomonas aeruginosa* (IAM 1514), *Brevundimonas diminuta* (IFO 14213), *Nocardia rubra* (IFM 18) and *Rhodococcus equi* (IFO 3730).

19. The process as claimed in claim 1, wherein $R^5$ represents hydrogen.

20. The process as claimed in claim 2, wherein $R^5$ represents hydrogen.

21. The process as claimed in claim 3, wherein $R^5$ represents hydrogen.

* * * * *